United States Patent [19]

Purdy et al.

[11] Patent Number: 5,215,528
[45] Date of Patent: Jun. 1, 1993

[54] CATHETER INTRODUCER ASSEMBLY INCLUDING NEEDLE TIP SHIELD

[75] Inventors: E. Robert Purdy, Fruit Heights; Timothy Erskine; Gerald H. Peterson, both of Salt Lake City; Stephen L. Thoresen, Orem, all of Utah

[73] Assignee: Becton, Dickinson and Company, Franklin Lakes, N.J.

[21] Appl. No.: 832,559

[22] Filed: Feb. 7, 1992

[51] Int. Cl.⁵ .......................................... A61M 5/178
[52] U.S. Cl. ...................................................... 604/164
[58] Field of Search ............... 604/164, 165, 166, 167, 604/168, 169, 170, 171, 110, 187, 198, 263, 53

[56] References Cited

U.S. PATENT DOCUMENTS

| | | | |
|---|---|---|---|
| 2,828,744 | 4/1958 | Hirsch et al. | 128/221 |
| 2,899,960 | 8/1959 | Ginsburg | 128/221 |
| 3,030,953 | 4/1962 | Koehn | 128/214 |
| 3,612,050 | 10/1971 | Sheridan | 128/214.4 |
| 4,160,450 | 7/1979 | Doherty | 128/214.4 |
| 4,237,882 | 12/1980 | Wickham | 128/218 |
| 4,610,671 | 9/1986 | Luther | 604/168 |
| 4,676,783 | 6/1987 | Jagger et al. | 604/171 |
| 4,747,831 | 5/1988 | Kulli | 604/110 |
| 4,762,516 | 8/1988 | Luther et al. | 604/164 |
| 4,778,453 | 10/1988 | Lopez | 604/110 |
| 4,781,692 | 11/1988 | Jagger et al. | 604/164 |
| 4,790,817 | 12/1988 | Luther | 604/53 |
| 4,790,828 | 12/1988 | Dombrowski et al. | 604/198 |
| 4,795,432 | 1/1989 | Karczmer | 604/110 |
| 4,816,024 | 3/1989 | Sitar et al. | 604/192 |
| 4,819,659 | 4/1989 | Sitar | 128/764 |
| 4,826,490 | 5/1989 | Byrne et al. | 604/198 |
| 4,832,696 | 5/1989 | Luther et al. | 604/164 |
| 4,846,811 | 7/1989 | Vanderhoof | 604/263 |
| 4,850,977 | 7/1989 | Bayless | 604/198 |
| 4,929,241 | 5/1990 | Kulli | 604/263 |
| 4,952,207 | 8/1990 | Lemieux | 604/164 |
| 4,955,866 | 9/1990 | Corey | 604/192 |
| 4,978,344 | 12/1990 | Dombrowski et al. | 604/198 |
| 4,990,141 | 2/1991 | Byrne et al. | 604/198 |
| 4,994,041 | 2/1991 | Dombrowski et al. | 604/164 |
| 5,015,242 | 5/1991 | Heifetz | 604/198 |
| 5,049,136 | 9/1991 | Johnson | 604/198 |
| 5,051,109 | 9/1991 | Simon | 604/263 |
| 5,053,017 | 10/1991 | Chamuel | 604/192 |
| 5,057,086 | 10/1991 | Dillard, III et al. | 604/195 |
| 5,059,180 | 10/1991 | McLees | 604/110 |
| 5,059,184 | 10/1991 | Dyke | 604/198 |
| 5,084,030 | 1/1992 | Byrne et al. | 604/198 |

*Primary Examiner*—John D. Yasko
*Attorney, Agent, or Firm*—Michael G. Schwarz

[57] ABSTRACT

An assembly for introducing a catheter into a blood vessel is provided. The assembly includes a needle hub having a needle secured thereto. The needle includes an elongate shaft having a bevelled tip. A portion of the needle shaft adjacent to the tip has a relatively large outside diameter. The shaft diameter of this portion exceeds the diameter of the shaft portion adjoining the tip and the diameter of the shaft portion extending between the enlarged shaft portion and the needle hub. A catheter is mounted over the shaft of the needle, and includes an inner surface which bears against the enlarged shaft portion. A substantially leak-proof seal is thereby provided between the catheter and the needle shaft. A needle tip cover is slidably mounted to the needle shaft and is engageable with the enlarged portion of the shaft to prevent its removal therefrom. The catheter is releasably mounted to the needle tip cover.

18 Claims, 5 Drawing Sheets

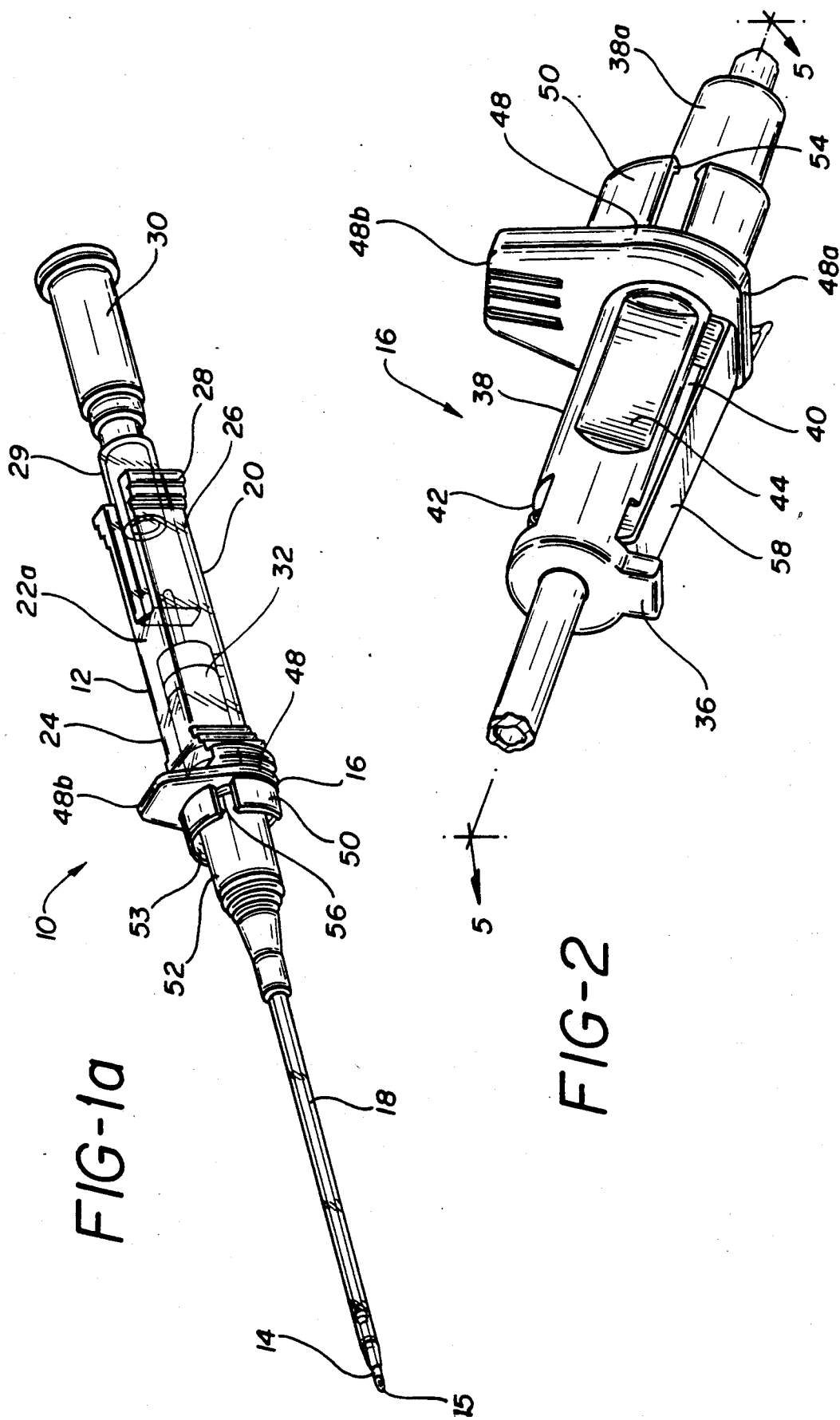

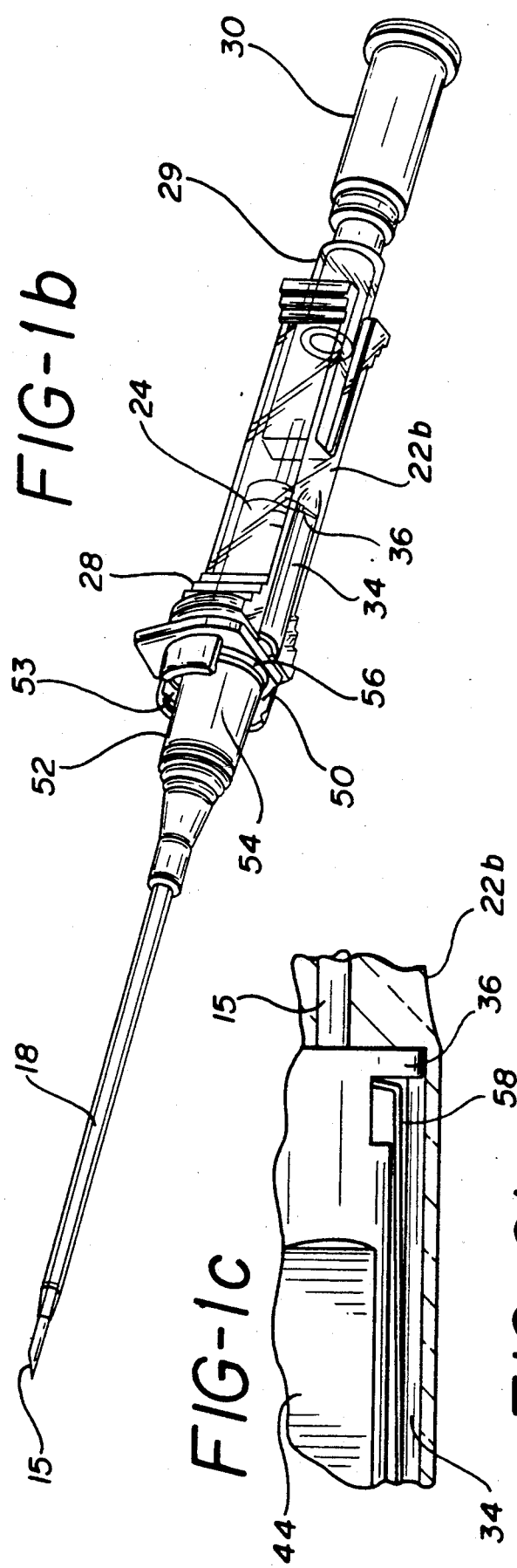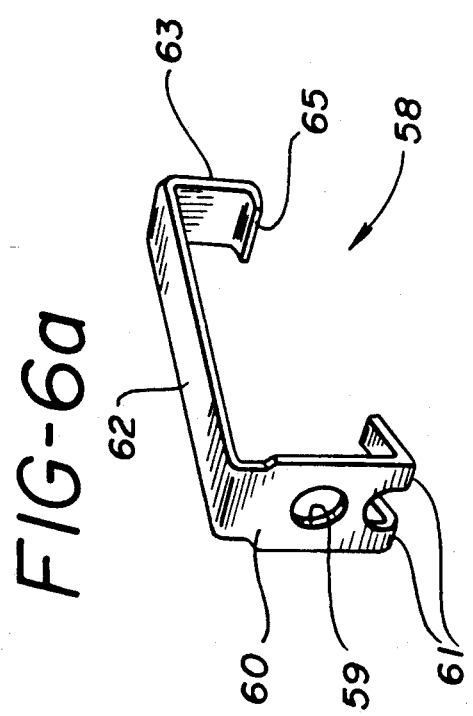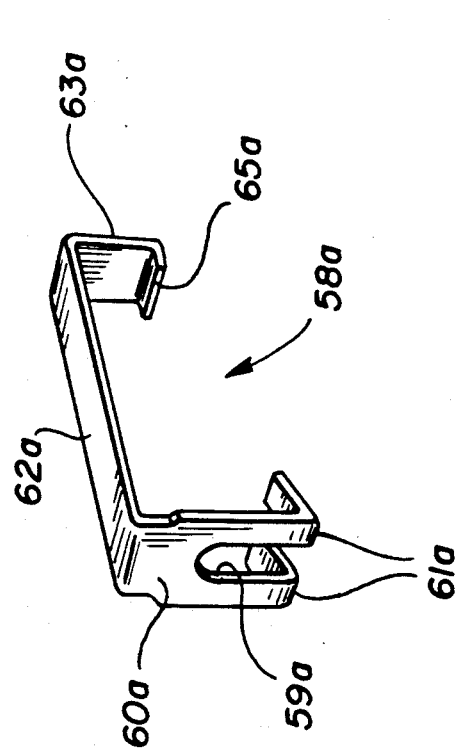

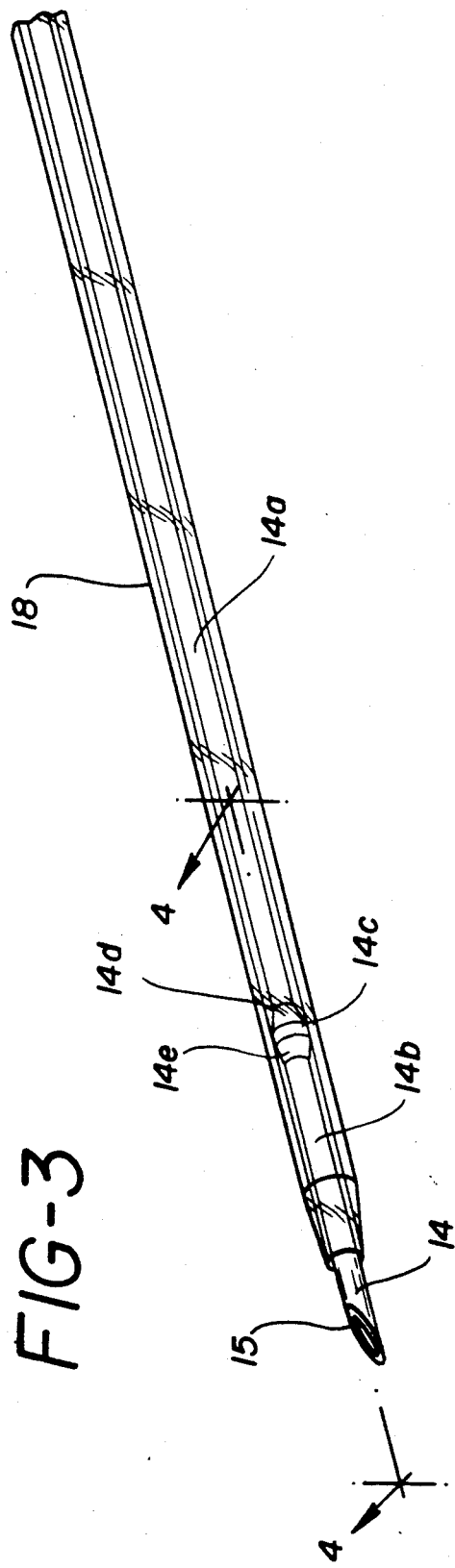
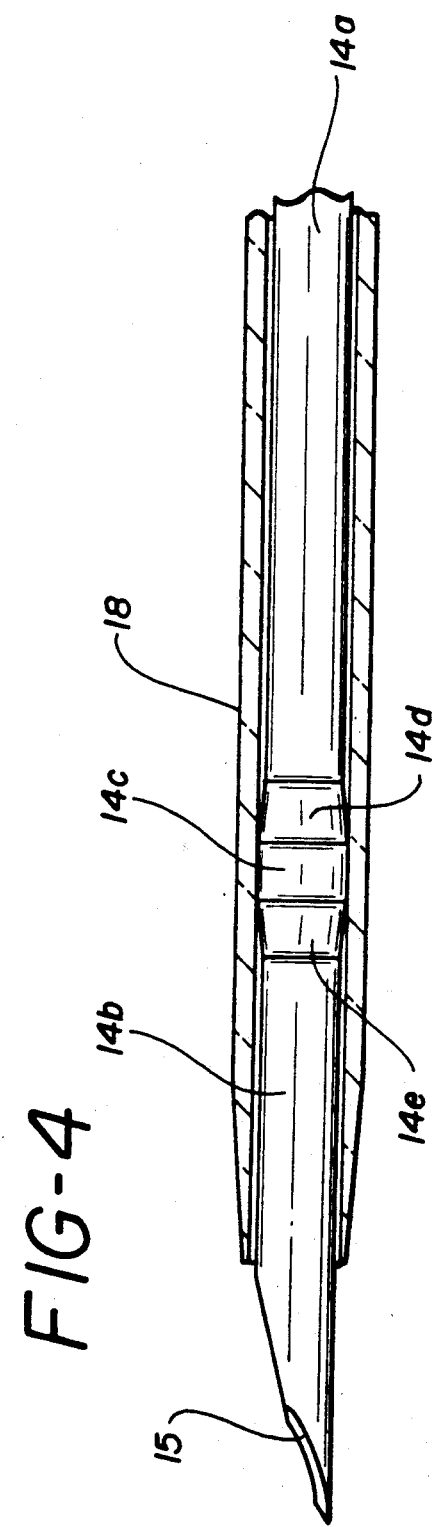

CATHETER INTRODUCER ASSEMBLY INCLUDING NEEDLE TIP SHIELD

BACKGROUND OF THE INVENTION

The invention relates to catheter introducer assemblies including means for protecting the user against needle sticks once the catheter is inserted into a blood vessel and the introducer needle is removed from the catheter.

A common technique for introducing catheters into blood vessels includes the steps of providing a catheter positioned over an introducer needle, inserting the needle and catheter into a blood vessel, and then withdrawing the needle from the catheter, leaving the catheter in place in the blood vessel. The withdrawal of the needle from the catheter causes the exposure of the tip of the needle. As the tip is quite sharp and is typically contaminated with bodily fluid, the needle may present a health risk unless steps are taken to cover the tip. A health risk is also presented by leakage of bodily fluid between the outside of the needle and the inside of the catheter. The present invention addresses both of these risks.

SUMMARY OF THE INVENTION

A catheter introducer assembly is provided which includes a needle having an elongate shaft secured to a needle hub, the shaft including a sharp tip, a first shaft portion adjoining the needle hub, a second shaft portion adjoining the tip, and a third shaft portion located between the first and second shaft portions, the third shaft portion having a larger outside diameter than the outside diameters of the first and second shaft portions. A catheter is mounted over the needle. The third shaft portion bears against the inner surface of the catheter, forming a substantially leak proof seal therewith. A cover is slidably mounted to the needle shaft. The third shaft portion is engageable with an engaging member. The engaging member permits the needle to slide inside the cover until the third shaft member meets the engaging member thus preventing the cover from being removed from the needle shaft.

The third shaft portion preferably has a substantially cylindrical configuration. A fourth shaft portion of substantially conical configuration preferably adjoins the third shaft portion at its larger end and the first shaft portion at its smaller end. The fourth shaft portion provides a smooth and uniform transition from the first shaft portion to the third portion, and forms the part of the third shaft portion which engages the blocking member.

BRIEF DESCRIPTION OF THE DRAWINGS

FIG. 1a is a top perspective view of a catheter introducer assembly according to a preferred embodiment of the invention;

FIG. 1b is a bottom perspective view of a catheter introducer assembly according to a preferred embodiment of the invention;

FIG. 1c is a detailed sectional view showing a portion of the needle cover within the needle hub;

FIG. 2 is an enlarged, bottom perspective view of the needle tip cover of the catheter introducer assembly;

FIG. 3 is an enlarged, top perspective view of the end portion of the catheter and needle shaft of the catheter introducer assembly;

FIG. 4 is an enlarged, cross sectional view thereof taken along line 4—4 of FIG. 3;

FIG. 6a is a perspective view of the preferred embodiment of the needle engaging member; and FIG. 6b is a perspective view of an alternative embodiment of the needle engaging member.

DETAILED DESCRIPTION

Figure 5A:
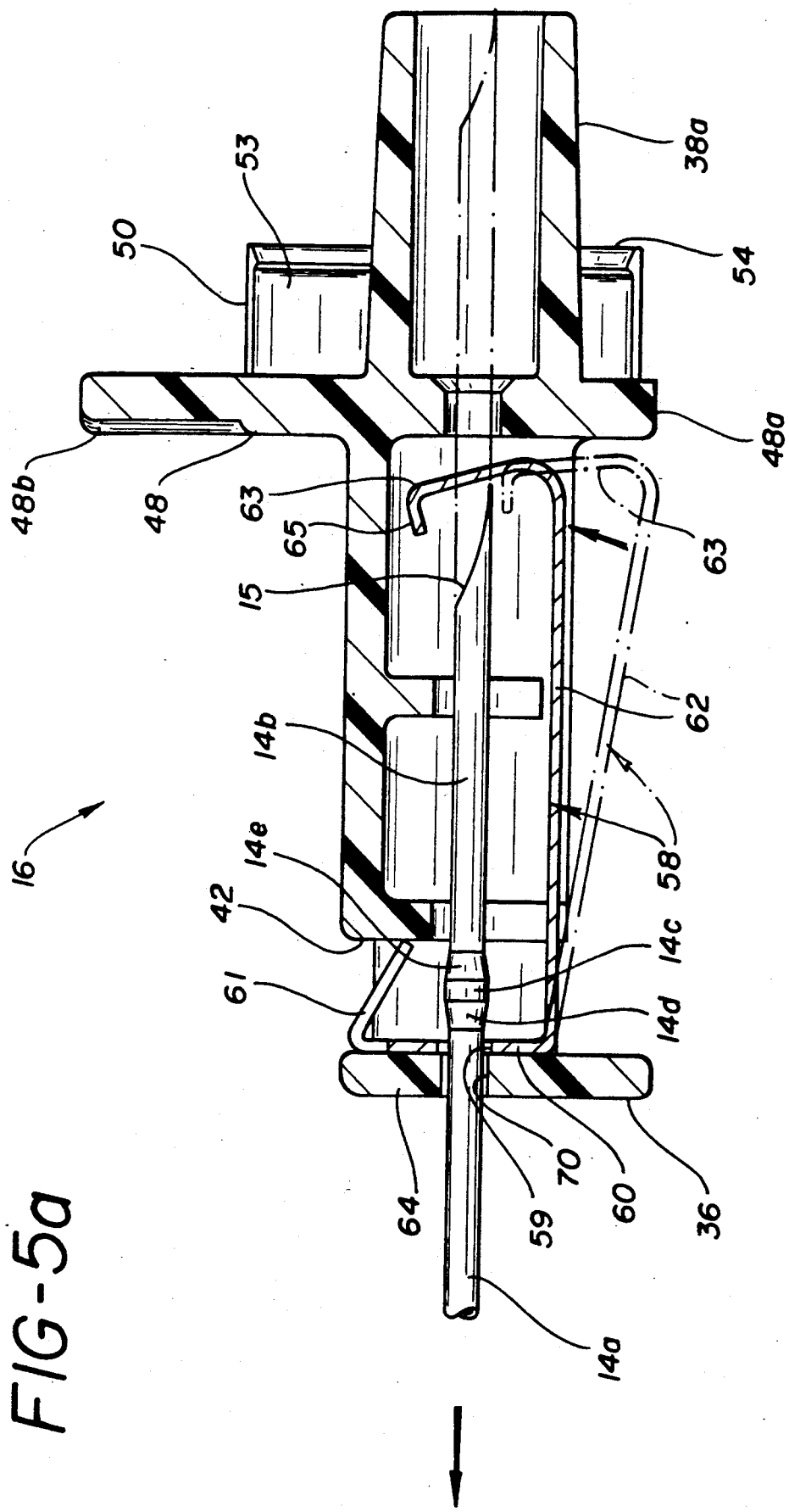
FIG. 5a is an enlarged cross sectional view of the preferred embodiment of the needle tip cover taken along line 5—5 of FIG. 2 showing the preferred embodiment of the needle engaging member.

A catheter introducer assembly 10 according to a preferred embodiment of the invention is shown in FIGS. 1a, 1b, 1c, 3, 4, 5a and 6a.

The introducer assembly 10 includes a needle hub 12, a needle 14, having a tip 15, secured to the needle hub, and a needle tip cover 16 slidably mounted to the shaft of the needle. A catheter 18 is slidably mounted to the needle shaft and releasably secured to the needle tip cover 16.

The needle hub 12 employed in accordance with the preferred embodiment of the invention includes an integrally molded, transparent body 20 having substantially planar top and bottom surfaces 22a, 22b and a pair of side walls 24, 26 which are generally concave to facilitate manipulation of the hub between the thumb and finger. Each end of the side walls includes a stepped portion 28. The rear end of the needle hub is bifurcated A cylindrical tube 29 extends through the bifurcated end portion and communicates with the rear end of the needle. A plug 30 may be secured to the rear end of the tube 29.

A cylindrical passage 32 is defined within the needle hub. The distal end of the needle tip cover 16 may be positioned within this passage, as shown in FIG. 1a. A slot 34 extends within hub 22 adjacent bottom surface 22b and adjoins the passage 32. (See FIG. 1c) The distal end of the needle tip cover 16 includes a radially extending projection 36 which extends and is slidable within the slot 34. The needle tip cover 16 is thereby prevented from rotating with respect to the needle hub 12 when mounted thereto.

The needle tip cover 16 includes an elongate, generally hollow body 38. A longitudinal slot 40 extends through one side of the body 38, as shown in FIG. 2, and rectangular opening 42 extends through the opposite side thereof. A pair of flat surfaces 44 defines portions of two other sides of the body.

A radially extending flange 48 extends from the body and adjoins one end of the longitudinal slot 40. The flange 48 has a generally annular configuration with the exception of a flat surface 48a on one side thereof and a tab 48b projecting from the opposite side. This tab 48b is provided to enable the user to push the tip cover and catheter away from the needle hub during insertion of the catheter and removal of the needle. A plurality of arcuate projections 50 extends from the flange 48, and together the arcuate projections define a receptacle 53 for retaining a catheter adapter 52. One end of the tubular body 38 defines a nose portion 38a for extending within the catheter adapter. The ends of the projections include inwardly projecting lips 54 for releasably retaining the flange 56 of the catheter adapter. Arcuate projections 50 and lips 54 are designed to engage flange 56 so that it is easier to push the tip cover away from the needle hub by means of tab 48b than it is to remove catheter adapter 52 from receptacle 53. The user is therefore discouraged from removing catheter adapter 52 and thus exposing needle tip 15 and is encouraged to use the passive shielding feature of the invention as further described herein.

A leaf spring 58, as best shown in FIGS. 5a and 6a, is mounted to the needle tip cover 16. The leaf spring 58 includes a flat body including a hole 59 in the flat first end wall 60 which surrounds the needle. The flat first end wall 60 extends generally perpendicularly to the longitudinal axis of the needle. Extending from flat portion 60 are bifurcations 61 which extend from the first end portion between two opposing walls bounding the rectangular opening 42.

Figure 5B:
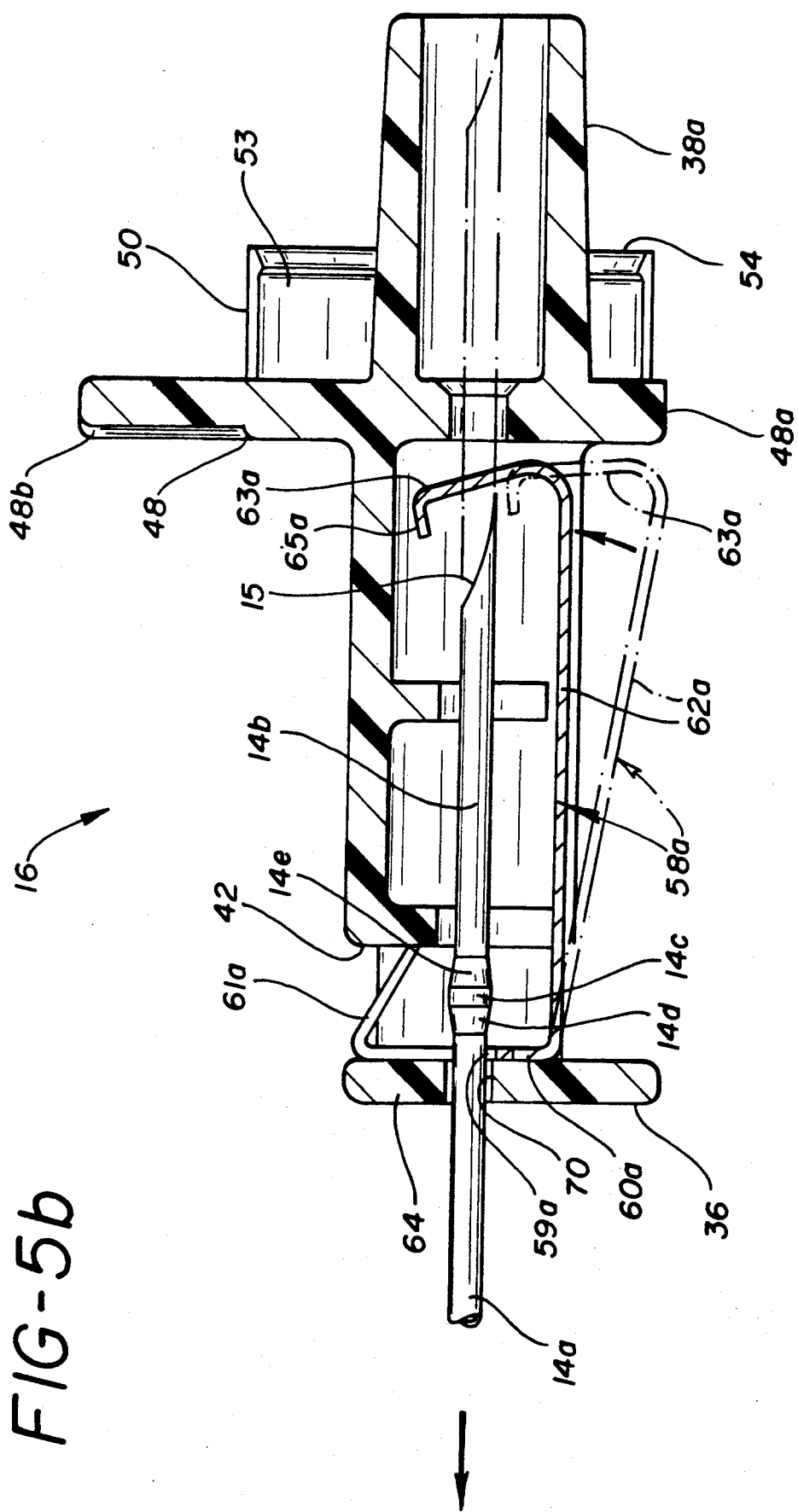
FIG. 5b is an enlarged cross-sectional view of the needle tip cover as in FIG. 5a but showing an alternative embodiment of the needle engaging member.

In an alternative embodiment shown in FIGS. 5b and 6b, the hole 59 in the end portion is replaced by bifurcations 61a, forming a saddle 59a which straddles the needle.

An elongate portion 62 of the leaf spring extends along the needle shaft. It is adjacent the radially extending flange 48 at one end and adjoins an end wall 64 of the tubular body 38 at the other end thereof. An inwardly extending transverse wall portion 63 of the spring having a generally L-shaped end extends from the elongate portion 62 towards the longitudinal axis of the needle 14. Transverse wall portion 63 is provided with lip 65. Portion 63 is resiliently urged towards the longitudinal axis when it bears against the needle shaft. This position is shown in FIG. 2. When the cover 16 is moved to a position where this portion of the spring moves past the tip 15 of the needle 14, as shown in FIG. 5, the bias of leaf spring 58 causes it to move from the position shown in phantom to that shown in solid lines. The path of needle 14 is blocked by extending wall portion 63 ad tip 15 is accordingly prevented from re-emerging from cover 16 by the transverse wall portion 63 of the spring 58 which forms a wall, blocking the exit path of needle tip 15.

The leaf spring 58 is preferably of integral construction, and made from stainless steel or other suitable material having the necessary memory characteristics. The elongate portion 62 of the spring extends outside the longitudinal slot 40 when it bears against the needle. A groove (not shown) may be provided in the radially extending flange 48 for guiding the transverse wall portion 63 of the spring towards the longitudinal axis of the needle.

The needle 14 is constructed to cooperate with both the needle tip cover 16 and the catheter 18. It includes a shaft having a sharp tip 15 at one end and a distal end which is secured to the needle hub 12. The distal end of the needle communicates with the chamber defined by the cylindrical tube 29.

Referring to FIG. 4, the needle 14 includes a first shaft portion 14a adjoining the needle hub 12 and a second shaft portion 14b adjoining the sharp tip 15. The first and second shaft portions have substantially the same outside diameters. A third shaft portion 14c is located between the first and second shaft portions. This shaft portion has a larger outside diameter than the first and second shaft portions. The diameter of the passage (not shown) extending through the shaft is substantially constant.

A fourth shaft portion 14d having a substantially conical configuration is provided between the first and third shaft portions. The larger end of the fourth shaft portion 14d adjoins the third shaft portion 14c. As shown in FIG. 4, the fourth shaft portion 14d provides a smooth and uniform transition from the first shaft portion to the third shaft portion of the needle.

A fifth shaft portion 14e may be positioned between the second and third needle shaft portions 14b, 14c. Like the fourth shaft portion 14d, it has a substantially conical configuration.

The third shaft portion 14c is located near the bevelled tip. Preferably it is about 0.004 inches larger in outside diameter than the nominal needle diameter, i.e. the diameter of the first and second shaft portions. Preferably it is may also be about 0.030 to about 0.12 inches in length.

The fourth shaft portion 14d is preferably about 0.015 to 0.045 inches in length, and is located about 0.3 inches from the end of the bevelled tip. As the overall needle length is between about 2.4 and 3.0 inches, the third and fourth shaft portions are substantially closer to the tip 15 than they are to the needle hub 12. The fifth shaft portion 14e may be substantially identical to the fourth shaft portion.

The shape and dimensions needle 14, including portions 14a-e as described herein are such that needle 14 can be easily inserted into and withdrawn from a vessel and catheter 18 can be readily slid off the needle.

The enlarged, third shaft portion 14c serves important functions. One is to provide a seal between the catheter 18 and the remainder of the needle shaft. The seal hinders blood leakage until the needle has been completely removed from the catheter. As shown in FIGS. 3 and 4, the tapered forward end of the catheter extends beyond the third shaft portion. This is designed to prevent blood from leaking past the third shaft portion as the needle penetrates a blood vessel.

Another important function of the enlarged, third shaft portion 14c is to prevent the needle tip cover 16 from being removed from the needle shaft. The diameter of this shaft portion, and that of a portion of the fourth shaft portion 14d, is accordingly slightly larger than the diameter of the opening 59 which extends through the end wall 60 of the leaf spring 58. The fourth shaft portion functions as an extension of the third shaft portion in that it is engageable with the portion of the end wall 60 surrounding the opening 59. When the needle 14 is withdrawn from the catheter 18 and the tip 15 is prevented from re-emerging from cover 16 by transverse wall portion 63, the diameter of third shaft portion 14 prevents needle 14 from being fully withdrawn from the needle tip cover and thus preventing needle tip 15 from being exposed.

The location of the enlarged shaft portion not only limits leakage between the catheter and needle as the needle penetrates a blood vessel. It also increases the stiffness of the needle in comparison to needles formed with enlarged tip portions.

As the needle tip cover 16 is releasably secured to the catheter adapter 52, it remains secured to the catheter adapter until the enlarged, fourth portion 14d of the needle shaft engages the end wall 60 of the leaf spring 58. This engagement prevents cove 16 from being removed from the needle 14 and traps the needle tip 15 in the cover 16 thus minimizing the risk of needle sticks. Further withdrawal of the hub from this point causes the needle tip cover to be detached from the catheter adapter. The introducer assembly is completely separated from the catheter 18 and discarded.

The needle tip cover 16 itself functions to secure needle tip 15. When needle tip 15 is drawn into needle tip cover 16, enlarged third shaft portion 14c is engaged by end wall 60 of leafspring 58. Hole 70 in needle tip cover 16 is, like hole 59, dimensioned to be larger in diameter than shaft 14, but smaller in diameter than enlarged portion 14c, so that it provides a second means of inhibiting the movement of needle tip 15 out of needle tip cover 16. Further, when needle 14 is pulled with a large force, end wall 60 may deform slightly. Wall 64 of needle tip cover 16 reinforces end wall 60 and thus reduces the risk of enlarged portion 14c popping through hole 59 If the alternative embodiment of spring 58a is used. wall 64 plays a more important role in that it engages enlarged portion 14c and prevents the removal of needle tip cover 16.

The enlarged area of the needle can be formed by electroetching material above and below this area to reduce the diameter of the remainder of the needle. Grinding is another alternative for shaping the needle to the desired configuration. Either technique provides a shaped needle of integral construction, which is preferred. Other possible techniques include plating the area selected for enlargement or insert molding a band of polymeric material around the needle.

In use, the introducer assembly 10 having the catheter 18 mounted over the needle 14 is grasped by the user between the stepped portions of the needle hub 12. The assembly is orientated such that the flat surface 48a and tab 48b of the flange 48 of the needle tip cover 16 are in opposing relation to the skin. The bevelled portion of the needle tip 15 will accordingly face outwardly with respect to the skin. The needle 14 is then inserted into a blood vessel. Flashback of blood can be observed within the transparent needle hub when the needle tip 15 is positioned within the vessel. The catheter 18 is then urged off the needle 14 in substantially the same way that such catheters are introduced into blood vessels using conventional catheter introducers which do not employ needle tip covers. Specifically, catheter adapter 52 is urged away from hub 12 by pressure on tab 48b and is thereby pushed off the needle a selected distance into the blood vessel. Catheter adapter 52 remains in receptacle 53 because of the interaction of flange 56 with lips 54. Thus, as catheter 18 is introduced into the vessel and needle 14 is withdrawn, needle tip 15 is automatically withdrawn into needle cover 16. Needle tip 15 is therefore passively shielded by the action of sliding catheter 18 into the vessel and off needle 14.

As the catheter 18 extends over the enlarged, third shaft portion 14c of the needle during both the introduction of the needle into the blood vessel and during most of the time while the catheter is pushed off the needle, leakage between the catheter and needle is substantially prevented. The frictional engagement between the third shaft portion 14c and the inner wall of the cannula portion of the catheter is noticeable as the catheter is moved off the needle.

As the needle tip cover is passively actuated, the user is not required to perform any operations outside of those employed using conventional over the needle catheter introducers. There is accordingly no need to learn any additional procedures in order to use the assembly 10 according to the invention. The combined actions of the spring 58 and enlarged needle shaft portion 14c cause the needle tip cover 16 to be permanently locked in place once the catheter insertion procedure has been completed. There is only minimal frictional engagement between the needle tip cover and the needle shaft and the needle hub 12. This insures that the cover will move with the catheter without becoming detached therefrom until the fourth shaft portion 14d engages the end wall 60 of the leaf spring 58.

The tip 15 of needle 14 is protected during the entire procedure described above subsequent to its introduction into the blood vessel. It is positioned within the catheter 18 when initially withdrawn and then finally positioned within the needle tip cover. Once the tip of the needle is withdrawn past the transverse wall portion 63 of the spring 58, the spring moves to the position shown in solid lines in FIG. 5. The needle tip cover is thereby prevented from being moved down the needle shaft towards the needle hub. The distance between the enlarged, third shaft portion 14c and the tip 15 of the needle 14 is less than the distance between the transverse wall portion 63 of the spring and the end wall 60 of the leaf spring 58. The third shaft portion 14c accordingly reaches the end wall 60 just after the spring moves over the tip of the needle. As this shaft portion 14c is unable to move through the smaller diameter opening 59 in the end wall 60, the needle tip cover 16 is prevented from being moved off the end of the needle.

Flange 48 also plays a role in preventing the needle tip 15 from re emerging from needle tip cover 16. If force is applied to pull needle tip cover back along needle 14 towards hub 22, needle tip 15 will tend to push against extending wall portion 63 which will tend to bend in a clockwise direction (see FIGS. 5a and b). If this happens, extending wall portion 63 will be prevented from further bending when it strikes the inside of flange 48. The exit path of needle tip 15 will thus be securely blocked.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A catheter introducing device comprising:
    a needle,
    a catheter tube mounted over the needle and slidable on the needle;
    a needle hub, the needle comprising an elongate shaft, a needle tip, a first shaft portion adjoining the needle hub, a second shaft portion adjoining the tip and a third shaft portion between the first and second shaft portions, wherein the third shaft portion has an outside diameter larger than the outside diameters of the first and second shaft portions, wherein the outside diameter of the third shaft portion is such that the third shaft portion does not substantially hinder the passage of the needle and catheter tube into and out of a vessel, and further wherein the catheter tube is slidable on the shaft over the third shaft portion.

2. The device of claim 1 wherein the shaft includes a fourth shaft portion having a substantially conical configuration, the fourth shaft portion including a first end having a relatively large outside diameter which adjoins and forms part of the third shaft portion and a second end having a relatively small outside diameter which adjoins the first shaft portion, the fourth shaft portion providing a smooth and uniform transition from the first shaft portion to the third shaft portion.

3. The device of claim 2 wherein the needle shaft includes a fifth shaft portion extending between the third shaft portion and the second shaft portion, the fifth portion having a substantially conical configuration.

4. The device of claim 1 wherein the third shaft portion is adapted to bear against the inside surface of the catheter and form a seal therewith.

5. The device of claim 1 wherein the third shaft portion is substantially closer to the tip of said needle than to said needle hub.

6. The apparatus of claim 1 wherein said third shaft portion has an outside diameter about 0.004 inches larger than the outside diameter of the first shaft portion.

7. The apparatus of claim 1 wherein said third shaft portion has a length between about 0.030 and 0.12 inches.

8. The device of claim 1 further comprising:
a needle tip cover, slidable on the shaft between a first position in which the needle tip is exposed and a second position in which the needle tip is shielded by the needle tip cover, the needle tip cover comprising engagement means for engaging the third shaft portion thus preventing the needle tip cover from sliding off the shaft.

9. The device of claim 8 wherein the needle tip cover comprises needle tip obstructing means for obstructing the needle tip when the needle tip cover is in the second position, so that when the needle tip cover is in the second position, the needle tip cover cannot be moved back to the first position.

10. The device of claim 9 wherein the needle obstructing means comprises a transverse wall which abuts the shaft when the needle tip cover is the first position and obstructs the needle tip when the needle tip cover is in the second position.

11. The device of claim 10 wherein the needle obstructing means comprises resilient means for automatically obstructing the needle tip when the needle tip cover is moved into the second position.

12. The device of claim 9 herein the needle tip cover comprises a front wall and the obstructing means abuts the front wall of the needle tip cover if the needle tip cover is moved towards the first position when the needle tip cover is in the first position.

13. The device of claim 11 wherein the needle obstructing means bears against the shaft when the needle tip cover is in the first position and moves transversely relative to the shaft in front of the needle tip when the needle tip cover is moved into the second position.

14. The device of claim 8 wherein the catheter includes a adapter at one end thereof, and wherein said needle tip cover includes holding means for releasably securing the adapter to said needle tip cover.

15. The device of claim 14 wherein said holding means is a receptacle comprising a generally circular wall extending substantially perpendicularly to the longitudinal axis of said needle and a plurality of arcuate projections extending from said wall, said wall including a substantially flat edge portion which adjoins said needle hub.

16. The device of claim 8 wherein said needle tip cover extends at least partially within said needle hub, said needle hub including means for preventing said needle tip cover from rotating about the longitudinal axis of said needle.

17. The device of claim 8 comprising a leaf spring, said leaf spring including an end portion positioned at least partially within said needle tip cover, said end portion being provided with a hole slightly larger than the diameter of the first shaft portion of said needle but smaller than the diameter of the third shaft portion of said needle, providing thereby a means to prevent said needle tip cover from sliding off the needle.

18. The device of claim 8 wherein the needle tip cover comprises a back wall, and the engagement means comprises the back wall.

* * * * *

(12) REEXAMINATION CERTIFICATE (4439th)
United States Patent
Purdy et al.

(10) Number: US 5,215,528 C1
(45) Certificate Issued: Sep. 11, 2001

(54) CATHETER INTRODUCER ASSEMBLY INCLUDING NEEDLE TIP SHIELD

(75) Inventors: E. Robert Purdy, Fruit Heights; Timothy Erskine; Gerald H. Peterson, both of Salt Lake City; Stephen L. Thoresen, Orem, all of UT (US)

(73) Assignee: Becton, Dickinson and Company

Reexamination Request:
No. 90/005,690, Mar. 31, 2000

Reexamination Certificate for:
Patent No.: 5,215,528
Issued: Jun. 1, 1993
Appl. No.: 07/832,559
Filed: Feb. 7, 1992

(51) Int. Cl.$^7$ .................................................. A61M 5/178
(52) U.S. Cl. ............................................................ 604/164
(58) Field of Search .................................. 604/164–171, 604/110, 187, 198, 263, 53

(56) References Cited

U.S. PATENT DOCUMENTS

| | | | |
|---|---|---|---|
| 4,755,170 | 7/1988 | Golden | 604/52 |
| 5,085,648 | 2/1992 | Purdy et al. | 604/198 |
| 5,135,504 | 8/1992 | McLees | 604/164 |

OTHER PUBLICATIONS

Defendant B. Braun Medical Inc.'s Memorandum in Support of its Motion to Stay Litigation Pending BD's Reexamination of Patent–In–Suit.
Becton Dickinson Plaintiff's Memorandum in Opposition to Defendant Braun's Motion to Stay Litigation Pending Reexamination of One of the Two Patents in Suit.
Defendant B. Braun Medical Inc.'s Reply Brief in Support of its Motion to Stay Proceedings.

*Primary Examiner*—Sharon Kennedy

(57) ABSTRACT

An assembly for introducing a catheter into a blood vessel is provided. The assembly includes a needle hub having a needle secured thereto. The needle includes an elongate shaft having a bevelled tip. A portion of the needle shaft adjacent to the tip has a relatively large outside diameter. The shaft diameter of this portion exceeds the diameter, of the shaft portion adjoining the tip and the diameter of the shaft portion extending between the enlarged shaft portion and the needle hub. A catheter is mounted over the shaft of the needle, and includes an inner surface which bears against the enlarged shaft portion. A substantially leak-proof seal is thereby provided between the catheter and the needle shaft. A needle tip cover is slidably mounted to the needle shaft and is engageable with the enlarged portion of the shaft to prevent its removal therefrom. The catheter is releasably mounted to the needle tip cover.

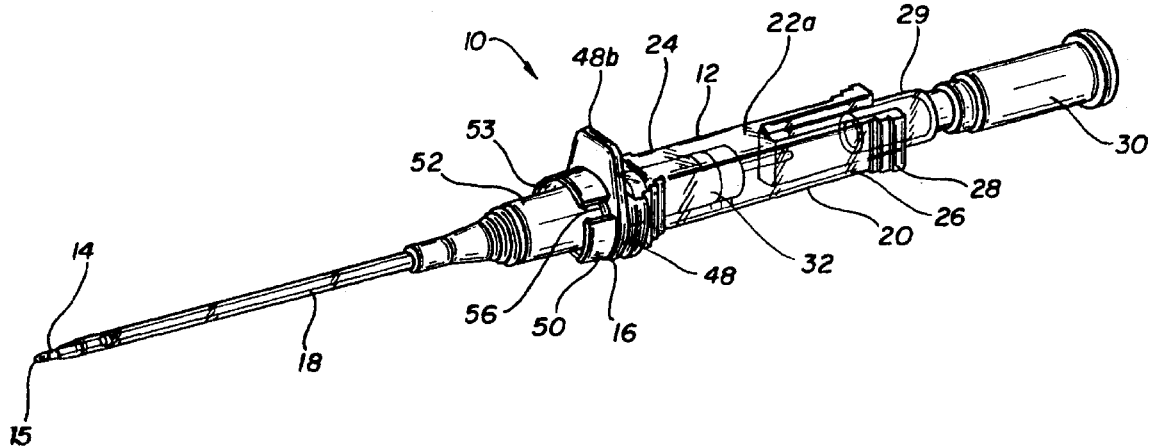

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–18 is confirmed.

* * * * *

(12) EX PARTE REEXAMINATION CERTIFICATE (6391st)
United States Patent
Purdy et al.

(10) Number: US 5,215,528 C2
(45) Certificate Issued: Aug. 19, 2008

(54) CATHETER INTRODUCER ASSEMBLY INCLUDING NEEDLE TIP SHIELD

(75) Inventors: E. Robert Purdy, Fruit Heights, UT (US); Timothy Erskine, Salt Lake City, UT (US); Gerald H. Peterson, Salt Lake City, UT (US); Stephen L. Thoresen, Orem, UT (US)

(73) Assignee: Becton, Dickinson and Company

Reexamination Request:
No. 90/008,460, Jan. 24, 2007

Reexamination Certificate for:
| | |
|---|---|
| Patent No.: | 5,215,528 |
| Issued: | Jun. 1, 1993 |
| Appl. No.: | 07/832,559 |
| Filed: | Feb. 7, 1992 |

Reexamination Certificate C1 5,215,528 issued Sep. 11, 2001

(51) Int. Cl.
*A61M 5/178* (2006.01)

(52) U.S. Cl. .................................................. 604/164.08
(58) Field of Classification Search ........................ None
See application file for complete search history.

(56) References Cited

U.S. PATENT DOCUMENTS

| | | | |
|---|---|---|---|
| 4,755,170 A | 7/1988 | Golden | |
| 4,964,854 A | 10/1990 | Luther | |
| 5,049,136 A | 9/1991 | Johnson | |
| 5,135,504 A | 8/1992 | McLees | |
| 5,558,651 A | 9/1996 | Crawford et al. | |

OTHER PUBLICATIONS

Documents from USPTO Reexamination Request File of U.S. Patent No. 5,215,528.

Excerpts from the Reissue of Crawford et al. U.S. Patent No. 5,601,536.

*Primary Examiner*—Beverly M. Flanagan

(57) ABSTRACT

An assembly for introducing a catheter into a blood vessel is provided. The assembly includes a needle hub having a needle secured thereto. The needle includes an elongate shaft having a bevelled tip. A portion of the needle shaft adjacent to the tip has a relatively large outside diameter. The shaft diameter of this portion exceeds the diameter, of the shaft portion adjoining the tip and the diameter of the shaft portion extending between the enlarged shaft portion and the needle hub. A catheter is mounted over the shaft of the needle, and includes an inner surface which bears against the enlarged shaft portion. A substantially leak-proof seal is thereby provided between the catheter and the needle shaft. A needle tip cover is slidably mounted to the needle shaft and is engageable with the enlarged portion of the shaft to prevent its removal therefrom. The catheter is releasably mounted to the needle tip cover.

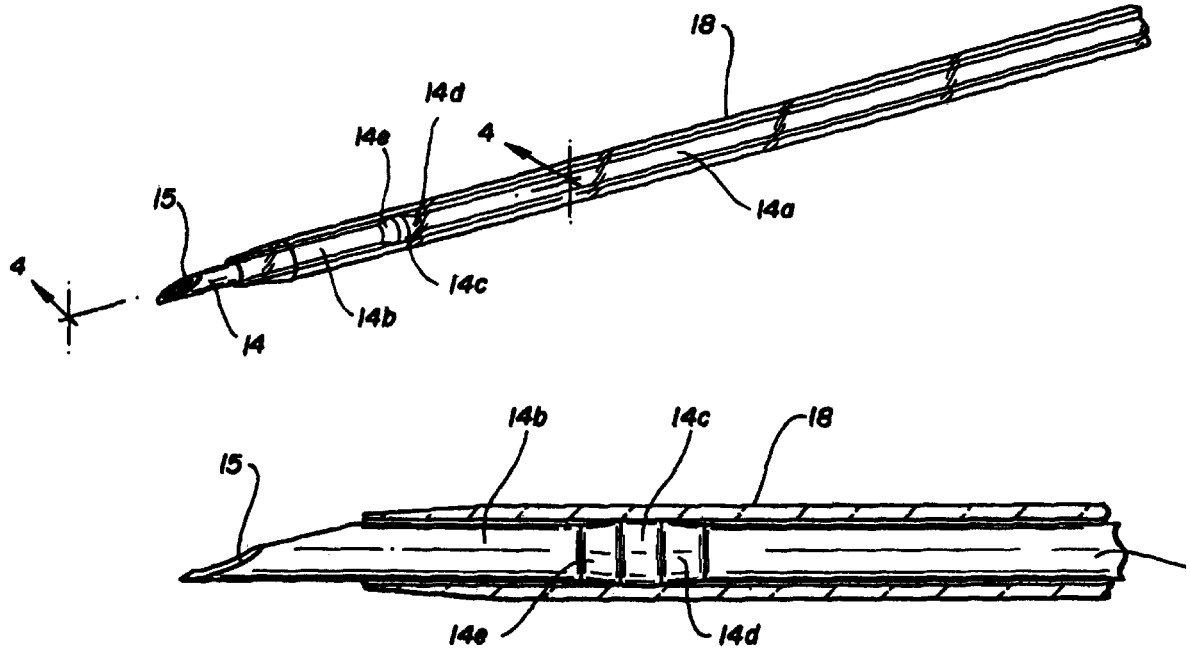

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 4 is cancelled.

Claim 1 is determined to be patentable as amended.

Claims 2, 3 and 5–18, dependent on an amended claim, are determined to be patentable.

1. A catheter introducing device comprising:
a needle,
a catheter tube mounted over the needle and slidable on the needle;
a needle hub, the needle comprising an elongate shaft, a needle tip, a first shaft poriton adjoining the needle hub, a second shaft portion adjoining the tip and a third shaft portion between the first and second shaft portions, wherein the third shaft portion has an outside diameter larger than the outside diameters of the first and second shaft portions, wherein the outside diameter of the third shaft portion is such that the third shaft portion does not substantially hinder the passage of the needle and *the* catheter tube into and out of a vessel, and further wherein the catheter tube is slidable on the shaft over the third shaft portion *and is adapted to bear against the inside surface of the catheter and form a seal therewith*.

* * * * *